United States Patent [19]

Znaiden et al.

[11] Patent Number: 5,523,090
[45] Date of Patent: * Jun. 4, 1996

[54] SKIN TREATMENT COMPOSITION

[75] Inventors: Alexander P. Znaiden, Trumbull; Craig S. Slavtcheff, Cheshire; Michael C. Cheney, Fairfield, all of Conn.

[73] Assignee: Chesebrough-Pond's USA Co., Division of Conopco, Inc., Greenwich, Conn.

[*] Notice: The portion of the term of this patent subsequent to Feb. 24, 2015, has been disclaimed.

[21] Appl. No.: 393,979

[22] Filed: Feb. 24, 1995

[51] Int. Cl.$^6$ .................................................. A61K 7/48
[52] U.S. Cl. ........................ 424/401; 514/846; 514/860; 514/944
[58] Field of Search ........................ 424/401; 514/860, 514/846, 944

[56] References Cited

U.S. PATENT DOCUMENTS

| | | | |
|---|---|---|---|
| 4,234,599 | 11/1980 | Van Scott et al. | 424/279 |
| 4,424,234 | 1/1984 | Alderson et al. | 424/317 |
| 4,612,331 | 9/1986 | Barratt et al. | 514/558 |
| 4,684,522 | 8/1987 | Marissal et al. | 424/195.1 |
| 4,839,161 | 6/1989 | Bowser et al. | 424/59 |
| 5,015,634 | 5/1991 | Siren | 514/103 |
| 5,019,566 | 5/1991 | Siren | 514/103 |
| 5,023,248 | 6/1991 | Siren | 514/103 |
| 5,030,451 | 7/1991 | Trebosc et al. | 424/401 |
| 5,037,803 | 8/1991 | Gueyne et al. | 514/2 |
| 5,051,411 | 9/1991 | Siren | 514/103 |
| 5,051,449 | 9/1991 | Kligman | 514/559 |
| 5,059,594 | 10/1991 | Sawai et al. | 514/103 |
| 5,082,833 | 1/1992 | Shamsuddin | 514/143 |
| 5,116,605 | 5/1992 | Alt | 424/401 |
| 5,194,259 | 3/1993 | Soudant et al. | 424/401 |
| 5,215,759 | 6/1993 | Mausner | 424/489 |
| 5,268,176 | 12/1993 | Znaiden et al. | 424/401 |
| 5,300,289 | 4/1994 | Garlich et al. | 424/54 |
| 5,362,494 | 11/1994 | Zysman et al. | 424/401 |
| 5,407,677 | 4/1995 | Tominaga et al. | 424/401 |

OTHER PUBLICATIONS

Abstract of FR 2 554 344—published May 10, 1987.
Abstract of DE 4 242 876—published Jun. 23, 1994.
Kligman, A., "Early Destructive Effect of Sunlight on Human Skin", JAMA, (Dec. 29, 1969), vol. 210, pp. 2377–2380.

Lavker, R., "Structural Alterations in Exposed and Unexposed Aged Skin", *Journal of Investigative Dermatology*, (1979), vol. 73, pp. 59–66.

Smith, J. et al., "Alterations in Human Dermal Connective Tissue with Age and Chronic Sun Damage", *Journal of Investigative Dermatology*, (1962), vol. 39, pp. 347–350.

Griffiths, Christopher E., et al., "Restoration of Collagen Formation in Photodamaged Human Skin by Tretinoin (Retinoic Acid)", *The New England Journal of Medicine* (1993), vol. 329, pp. 530–535.

Estee Lauder "Double Edition Thigh Zone" anti-cellulite product label.

Avon "New Figure Multi-Action Body Creme" product label.

Shuster, S. et al., "The Influence of Age and Sex on Skin Thickness, Skin Collagen and Density", *British Journal of Dermatology*, (1975), vol. 93, pp. 639–643.

Chen, S. et al., "Effects of All-Trans Retinoic Acid on UVB-Irradiated and Non-Irradiated Hairless Mouse Skin", *Society for Investigative Dermatology*, (1992), vol. 98, pp. 248–254.

Nakagawa, et al., "Long-Term Culture of Fibroblasts in Contracted Collagen Gels: Effects on Cell Growth and biosynthetic Activity", The Society for Investigative *Dermatology, Inc.*, (1989), vol. 93, pp. 792–798.

Jutley, J. K. et al., "Influence of Retinoic Acid and TGF-β on Dermal Fibroblast Proliferation and Collagen Production in Monolayer Cultures and Dermal Equivalents", *Matrix*, (1993), vol. 13, pp. 235–241.

*Primary Examiner*—Jyothsan Venkat
*Attorney, Agent, or Firm*—Rimma Mitelman

[57] ABSTRACT

Skin treatment compositions for improving skin strength and firmness and reducing signs of cellulite. The compositions contain a xanthine (e.g., caffeine or theophylline) and an inositol phosphoric acid, and/or alpha hydroxy acid. The ratio of the xanthine to the acid is in a specific range to maintain the xanthine in a solubilized state. A method of preventing or reducing the signs of cellulite by applying a mixture of an inositol phosphoric acid and an alpha hydroxy acid is also disclosed.

11 Claims, No Drawings

SKIN TREATMENT COMPOSITION

FIELD OF THE INVENTION

The invention relates to skin treatment compositions containing an inositol phosphoric acid and an alpha hydroxy, alone or in combination with a xanthine in a specific ratio and the use of the compositions for improving the condition and appearance of mammalian skin.

BACKGROUND OF THE INVENTION

In recent years cosmetic compositions which improve the appearance of skin have become popular with consumers. There is, at the present time, a demand for cosmetic compositions which reduce the appearance, i.e., the outward indications or signs, of cellulite.

Cellulite is a lay term describing the uneven texture of skin in specific areas of the female body, primarily the hips, thighs, and buttocks. The prevalence of cellulite is high, estimated between 50% and 80% of the female population. Virtually no cellulite has been observed in men with normal androgen levels. The severity of cellulite tends to worsen with obesity, although it is easily observable in women with a below average body mass index, as well as with age, although postmenopausal women report a reduction in cellulite.

Premenopausal females tend to store fat subcutaneously, primarily in the gluteal/thigh areas where cellulite is most common. The elevation in androgen levels postmenopausally results in a dramatic shift in fat storage patterns. Fat is stored in the visceral and subcutaneous depots of the abdomen, more similar to male fat storage patterns, explaining the reduction in cellulite symptoms of postmenopausal women. Triglyceride is stored in individual adipocytes which are grouped into capillary rich lobules. Thin, vertical septa of connective tissue separate the lobules and tether the overlying superficial fascia to the underlying muscle.

The dimpling/bumpy appearance of cellulite is a result of the deformation of the aforementioned lobules as a result of outward forces on the adipose tissue (e.g., muscle flexing resulting in a localized outward pressure, pull of gravity). These lobules are large (up to 1 cm wide) and easily protrude into the overlying dermis, causing a visible deformation on the surface of the skin that presents itself as cellulite. As the connective septa run in the same direction as these outward forces, they can offer no counter force to keep the adipose from deforming into the dermis.

Net fat storage or removal within the adipocyte is dependent on a balance between uptake of dietary triglycerides circulating in the blood via chylomicrons and breakdown of stored triglyceride within the adipocyte and removal of free fatty acids for subsequent energy utilization. Lipolysis (breakdown of triglyceride within the adipocyte), occurs when hormone sensitive lipase (HSL) is activated. HSL activation requires phosphorylation via a cAMP (cyclic adenosine monophosphate) dependent protein kinase. As such, cAMP level is rate limiting to lipolysis. Net level of cAMP is a result of a balance between its enzymatic synthesis from adenosine triphosphate (ATP) via adenylate cyclase and its breakdown via phosphodlesterases. Adipocytes express both beta and alpha-2 receptors, which both activate and inactivate, respectively, adenylate cyclase.

Most cellulite treatments focus on lipolysis as the primary mode of action. Soudant et al. (U.S. Pat. No. 5,194,259) teach anti-cellulitis composition using an alpha-2 blocker, theoretically stimulating lipolysis. A number of patents cite use of xanthines (e.g., caffeine and derivatives) as phosphodiesterase inhibitors (French Patent No. 2,499,405; French Patent No. 2,554,344; Marissal et al., U.S. Pat. No. 4,684,522; Trebose et al., U.S. Pat. No. 5,030,451). Unfortunately, these products have not had great success in the marketplace, presumably due to poor efficacy. This may be a result of the fact that caffeine and xanthines in general have very limited solubility in water and the drug's activity in a typical cosmetic preparation (e.g., oil in water emulsion) would be very low due to poor penetration as it is bound in a crystallized form in the product.

Alpha hydroxy acids are emerging as accepted ingredients for improving the appearance of dry, flaky, wrinkled, aged, photodamaged skin and for treating various disorders of skin, e.g., hyperkeratosis, ichthyosis, skin blemished, acne, warts, herpes, psoriasis, eczema, pruritis. See e.g., U.S. Pat. No. 4,234,599 (Van Scott et al.), U.S. Pat. No. 4,612,331 (Barratt et al.), U.S. Pat. No. 4,424,234 (Alderson et al.), U.S. Pat. No. 4,839,161 (Bowser et al.).

The use of inositol phosphoric acid compounds in skin treatment compositions is also known, albeit to a much lesser extent. For example, U.S. Pat. No. 5,268,176 (Znalden et al.) discloses the topical application of an inositol phosphoric acid for treatment of a dermatological condition commonly known as spider veins. U.S. Pat. No. 5,116,605 (Alt) dicloses compositions including phytic acid (also known as "inositol hexaphosphate") for mitigating male pattern baldness and testosterone-induced acne. DE 4242876 (Beiersdorf) discloses cosmetic compositions containing citric acid, biotin, and phytic acid as an anti-oxidant.

The use of xanthines, e.g., caffeine and/or theophylline, in cosmetic compositions is also known, particularly as lipolytic agents for cellulite treatment. For instance, U.S. Pat. No. 5,215,759 (Mausner) discloses anti-cellulite compositions based on a specific combination of five ingredients and which may optionally include caffeine and sodium lactate. U.S. Pat. No. 5,362,494 (Zysman et al.) discloses cosmetic compositions containing xanthines as liporegulators and hydroxy acids, in particular glycolic acid, as a deplgmenting agent. U.S. Pat. No. 5,037,803 (Guyene et al.) discloses cosmetic compositions which may include theophylline or caffeine and lactic acid. Compositions containing an inositol phosphoric acid described in the above-cited Znaiden et al. '176 patent may also include xanthines.

The art discussed above does not envision a method of reducing the appearance of cellulite by increasing the strength and firmness of epidermal and dermal layers of the skin, which in turn results in an increased support for the underlying tissue. Rather, the anti-cellulite art focuses on the treatment of cellute via lipolysis. Additionally, the transdermal delivery of xanthines and, consequently, their efficacy, is limited by their poor solubility in aqueous-based or ethanol-based cosmetic compositions, and the art discussed above does not address the need for solubilizing xanthines and does not envision skin treatment compositions based on a specific combination of a xanthine with an alpha hydroxy acid or an inositol phosphoric acid according to the present invention.

Accordingly, it is an object of the present invention to provide a method of reducing the appearance of cellulite by applying to cellulite-affected skin ingredients for treating layers of skin tissue above subcutaneous fat.

It is an object of the present invention to provide skin treatment compositions containing a solubilized xanthine in a water-based or water/solvent-based mixture.

It is another object of the invention to provide compositions containing an alpha hydroxy acid in combination with a xanthine.

It is yet another object of the invention to provide compositions containing an inositol phosphoric acid in combination with a xanthine.

It is still another object of the invention to provide a method for preventing or reducing the appearance of cellulite by applying to the skin a composition containing a xanthine in combination with an inositol phosphoric acid and/or an alpha hydroxy acid.

It is another object of the present invention to provide a method of reducing the appearance of cellulite by applying to cellulite-affected skin a composition containing a combination of an inositol phosphoric acid and an alpha hydroxy acid.

These and other objects of the invention will become more apparent from the detailed description and examples that follow.

SUMMARY OF THE INVENTION the above objects are attained by the present invention which includes, in part, a skin treatment composition containing an alpha hydroxy acid and/or an inositol phosphoric acid in combination with a xanthine. The present invention is based at least in part on the discovery that certain acids, e.g., an alpha hydroxy acid or an inositol phosphoric acid, solubilize a xanthine when the ratio of the xanthine to the acid is in a specific range according to the invention. In its first aspect, the present invention provides compositions containing a xanthine and an alpha hydroxy acid, wherein the weight ratio of the xanthine to the acid is in the range of from about 1:1,000 to about 4:1. In its second aspect, the present invention provides compositions containing a xanthine and an inositol phosphoric acid wherein the weight ratio of the xanthine to the acid is in the range of from about 1:1,000 to about 4:1.

According to the present invention, by virtue of combining a xanthine with an alpha hydroxy acid and/or an inositol phosphoric acid in specific ratio, the performance of the compositions is substantially improved.

The present invention also includes a method of preventing or reducing cellulite, which method includes applying to the skin a composition containing an inositol phosphoric acid and/or an alpha hydroxy acid and a xanthine wherein the weight ratio of the xanthine to the acid is in a specific range according to the invention.

In yet another aspect of the present invention, the invention also includes a method of preventing or reducing cellulite by applying to skin a composition containing an inositol phosphoric acid and an alpha hydroxy acid.

Compositions of the invention are intended for topical application to mammalian skin which is already affected by cellulite, or, in the alternative, the inventive compositions may be applied prophylactically to normal healthy skin to prevent or reduce the signs of cellulite.

DETAILED DESCRIPTION OF THE INVENTION

The first essential ingredient of the inventive compositions is a xanthine. The term "xanthine" as used herein includes the following compounds:

xanthine ($C_5H_4O_2N_4$);

1,3-dimethyl xanthine (commonly known as "theophylline");

3,7-dimethyl xanthine (commonly known as "theobromine");

trimethyl xanthine (commonly known as "caffeine");

alloxantin;

paraxanthine;

heteroxanthine;

salts of the above mentioned compounds (e.g., ethylenediamine salts of theophylline);

and mixtures thereof.

The preferred xanthine included in the inventive compositions is caffeine and/or theophylline due to their availability and optimum efficacy.

The xanthine is present in the inventive compositions preferably in an amount of at least 0.05%, generally in the amount of from 0.05% to 20%, preferably in the amount of from 0.10% to 10%, optimally in the amount of from 0.5% to 3.0% by weight of the composition in order to maximize efficacy at optimum cost.

According to the first embodiment of the invention, the second essential ingredient of the inventive compositions is an inositol phosphoric acid, which may be one or a combination of a mono-, di-, tri-, tetra-, penta-, or hexa-phosphate of inositol. Inositol is also known as 1,2,3,4,5,6-hexahydrocyclohexane and 1,2,3,4,5,6-cyclohexanehexol. Most preferred is inositol hexaphosphate (otherwise known as phytic acid) due to its low cost and high efficacy. Salts of phytic acid are also suitable, e.g., a water-soluble salt of phytic acid selected from the group consisting of alkali metal, alkaline earth metal, ammonium and $C_2$-$C_{12}$ alkanolammonium salts. For further descriptions of these phosphates, attention is drawn to U.S. Pat. No. 5,051,411 herein incorporated by reference. Preferably, the inositol phosphoric acid is present in the inventive compositions in an amount of at least 0.5%, generally in an amount of from 0.75% to 25%, optimally in an amount of from 2.5% to 12% to optimize the anti-cellulite efficacy.

According to the first embodiment of the invention, the ratio of the xanthine to the inositol phosphoric acid is in the range of from 1:1,000 to 4:1, preferably in the range of from 1:50 to 2:1, most preferably in the range of from 1:32 to 1:1 in order to optimize the solubility of the xanthine and the performance of the inventive compositions.

According to the second embodiment of the invention, the second essential ingredient of the inventive compositions is an alpha hydroxy acid having the following general structure:

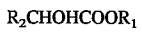

wherein $R_1$ and $R_2$ are H, alkyl, arylalkyl or aryl, straight or branched chain or cyclic form, having 1 to 20 carbon atoms, and in addition $R_2$ may carry OH, CHO, COOH and alkoxy group having 1 to 9 carton atoms.

The typical alkyl, aralkyl and aryl groups for $R_1$ and $R_2$ include methyl, ethyl, propyl, isopropyl, butyl, pentyl, octyl, lauryl, stearyl, benzyl and phenyl, etc.

Examples of suitable alpha hydroxy acids include but are not limited to:

alpha hydroxy acetic acid (also known as "glycolic acid")

alpha hydroxybenzeneacetic acid (also known as "mandelic acid")

alpha hydroxypropionic acid (also known as "lactic acid")

alpha hydroxybutanoic acid alpha hydroxyhexanoic acid alpha hydroxyoctanoic acid (also known as "alpha hydroxy caprylic acid")
alpha hydroxynonanoic acid
alpha hydroxydecanoic acid
alpha hydroxyundecanoic acid
alpha hydroxydodecanoic acid (also known as "alpha hydroxy lauric acid")
alpha hydroxytetradecanoic acid
alpha hydroxyhexadecanoic acid
alpha hydroxyoctadecanoic acid
alpha hydroxyoctaelcosanoic acid;
dicarboxylic alpha hydroxy acids:
dihydroxybutanedioic acid (tartaric acid)
2-hydroxybutanedioic acid (malic acid)
2-hydroxy propanedioic acid
2-hydroxy hexanedioic acid
2-hydroxy octanedioic acid
2-hydroxy decanedioic acid
2-hydroxy dodecanedioic acid
2-hydroxy myristicdioic acid
2-hydroxy palmitiodioic acid
Tricarboxylic alpha hydroxy acids:
2-hydroxy-1,2,3,-propanetricarboxylic acid (citric acid)
1-hydroxy-1,2,3,-propanetricarboxylic acid (isocitric acid)
and mixtures thereof.

The preferred alpha hydroxy acids are water soluble, since the particular utility of the inventive compositions lies in improving transdermal delivery of caffeine from water-based or water and solvent based cosmetic compositions by virtue of solubilizing caffeine.

Salts of alpha hydroxy acids (e.g., potassium, sodium, ammonium, triethanolammonium salts) are also meant to be included within the term "alpha hydroxy acid". Depending on the pH of the composition, a mixture of the salt and the acid is present.

The preferred alpha hydroxy acids are monocarboxylic acids, in order to improve skin penetration and efficacy.

Even more preferably, the hydroxy acid is chosen from lactic acid, glycolic acid, mandelic acid, and mixtures thereof to optimize the efficacy of compositions by increasing percutaneous absorption. In the most preferred embodiment of the invention, in order to maximize the performance of hydroxy acid, inventive compositions contain the L-form of an alpha hydroxy acid.

Preferably the amount of the alpha hydroxy acid component present in the composition according to the invention is from 1.5 to 20%, more preferably from 1.5 to 15% and most preferably from 3.0 to 12.0% by weight of the composition.

The weight ratio of the xanthine to the alpha hydroxy acid is in the range of from 1:1,000 to 4:1, preferably in the range of from 1:50 to 2:1, most preferably in the range of from 1:24 to 1:1, in order to maximize the solubility of the xanthine and to optimize the performance of the inventive compositions.

In the preferred embodiment of the invention, the inventive compositions include, in addition to a xanthine, both an alpha hydroxy acid (most preferably lactic and/or glycolic acid), and an inositol phosphoric acid (most preferably phytic acid).

The compositions according to the invention are used to improve the appearance of skin by increasing skin strength, firmness and elasticity and preventing or reducing the appearance of cellulite.

According to another embodiment of the invention a method of preventing or reducing the appearance of cellulite includes applying to skin a composition containing from about 0.75% to about 25% of an inositol phosphoric acid (preferably 2.5% to 12%, most preferably from about 2.5% to about 12%) and from about 1.5% to about 25% (preferably from about 1.5% to about 15%, most preferably from about 3% to about 12%) of an alpha hydroxy acid in a cosmetically acceptable vehicle. The preferred inositol phosphoric acid is phytic acid and the preferred alpha hydroxy acid is selected from the group consisting of lactic acid, glycolic acid, mandelic acid, and mixtures thereof to optimize the efficacy of compositions. In the most preferred embodiment of the invention, in order to maximize the performance of hydroxy acid, inventive compositions contain the L-form of a mono-carboxylic alpha hydroxy acid.

The compositions according to the invention also comprise a cosmetically acceptable vehicle to act as a dilutant, dispersant or carrier for the active components in the composition, so as to facilitate their distribution when the composition is applied to the skin, hair and/or nails.

In the preferred embodiment of the invention, a cosmetically acceptable vehicle is comprised either of water or of a water/solvent blend. The solvent is optimally chosen from propylene glycol, ethanol, butylene glycol, and polyethylene glycols of various molecular weights.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from 5 to 99.9%, preferably from 25 to 80% by weight of the emulsion, and can, in the absence of other cosmetic adjuncts, form the balance of the composition.

OPTIONAL SKIN BENEFIT MATERIALS AND COSMETIC ADJUNCTS

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Actives are defined as skin benefit agents other than emollients and other than ingredients that merely improve the physical characteristics of the composition. Although not limited to this category, general examples include sunscreens, tanning agents, skin anti-wrinkling agents, anti-inflammatory agents, skin lighteners and moisturizers.

Sunscreens include those materials commonly employed to block ultraviolet light. Illustrative compounds are the derivatives of PABA, and cinnamate. For example, octyl methoxycinnamate and 2-hydroxy-4-methoxy benzophenone (also known as oxybenzone) can be used. Octyl methoxy-cinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Suitable anti-inflammatory compounds include but are not limited to rosmarinic acid, glycyrrizinate derivatives, alpha bisabolol, azulene and derivatives thereof, aslaticoside, sericoside, ruscogenin, escin, escolin, queratin, rutin, betulinic acid and derivatives thereof, catechin and derivatives thereof.

Suitable vasoacitive compounds include but are not limited to papaverine, yohimbine, visnadin, khellin, bebellin, nicotinate derivatives.

Suitable skin whitening compounds include but are not limited to ferulic acid and/or kojic acid.

Anti-wrinkling compounds include but are not limited to alpha hydroxy acids, retinol and derivatives, tocopherol and derivatives, salicylates and derivatives.

Surfactants, which are also sometimes designated as emulsifiers, may be incorporated into the cosmetic compositions of the present invention. Surfactants can comprise anywhere from about 0.5% to about 30%, preferably from about 1% to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, avaliable under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trillnoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds.

For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, sequalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality. Cellulosic derivatives may also be employed, e.g., hydroxypropyl cellulose (Klucel HI®).

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, proplonate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

The composition according to the invention is intended as a product for topical application to human skin, especially as an agent for reducing or preventing the appearance of cellulite, for improving the firmness and elasticity of skin and generally to enhance the quality and flexibility of skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

The topical skin treatment composition of the invention can be formulated as a lotion having a viscosity of from 4,000 to 10,000 mPas, a fluid cream having a viscosity of from 10,000 to 20,000 mPas or a gel having a viscosity of from 20,000 to 100,000 mPas or above. The composition can be packaged in a suitable container to suit its viscosity and intended use by the consumer. For example, a lotion or fluid cream can be packaged in a bottle or a container fitted with a pump suitable for finger operation. When the composition is a gel, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLES

Solubility of various xanthines was investigated in the presence of various acids in Examples 1–9.

Example 1

2% theophylline (Knoll Pharmaceuticals—BASF) was added to 88 grams of water at room temperature. Various acids as indicated in Table 1 were added at 10% concentration to make a total batch of 100 grams.

TABLE 1

| Sample | Acid | Wt. ratio xanthine: acid | OBSERVATIONS Initial | 3 days |
|---|---|---|---|---|
| A | Control | | cloudy/precipitate | cloudy/precipitate |
| B | 10% glycolic acid (76%) | 0.285 | clear | clear |
| C | 10% L-lactic acid (88%) | 0.227 | clear | clear |
| D | 10% malic acid (D-L) | 0.200 | clear | clear |
| E | 10% tartaric acid | 0.200 | clear | clear |
| F | 10% citric acid | 0.200 | clear | crystals formed |
| G | 10% mandelic acid | 0.200 | clear | clear |
| H | 10% phytic acid (50%) | 0.400 | clear | clear |
| I | 10% phosphoric acid (45%) | 0.444 | cloudy/precipitate | cloudy/precipitate |
| K | 10% hydrochloric acid (20%) | 1.00 | cloudy/precipitate | cloudy/precipitate |

The results in Table 1 demonstrate that alpha hydroxy acids (Samples B–G) and phytic acid (Sample H) solubilized caffeine, while inorganic acids (Samples I and K) did not solubilize caffeine. Caffeine was not solubilized in Sample A (which did not contain any acid) either.

Example 2

Example 1 was repeated with 10% lactic acid except that the pH of the mixtures was varied (using KOH) as indicated in Table 2. The results that were obtained are summarized in Table 2 below.

TABLE 2

| Sample | Molar ratios lactic/K-lactate | pH | OBSERVATIONS Initial | 3 days |
|---|---|---|---|---|
| A | .195/0 | 2.04 | clear | clear |
| B | 3.5/1 | 3.50 | clear | clear |
| C | 2.0/1 | 4.03 | clear | clear |
| D | 1.75/1 | 5.50 | clear | clear |
| E | 1.2/1.0 | 5.98 | cloudy/precipitate | cloudy/precipitate |

Example 3

Example 2 was repeated except that 10% phytic acid at various pH was employed. The results that were obtained are summarized in Table 3.

TABLE 3

| Sample | Molar ratios phytic/K-phytate | pH | Initial | 3 days |
|---|---|---|---|---|
| A | .0151/0 | .87 | clear | clear |
| B | .280/1 | 1.50 | clear | clear |
| C | .184/1 | 2.67 | clear | clear |
| D | .156/1 | 4.59 | clear | clear |
| E | .142/1 | 5.5 | clear | clear |
| F | .127/1 | 6.5 | cloudy/precipitate | cloudy/precipitate |

The results in Tables 2 and 3 demonstrate that the pH of the inventive compositions is preferably 5.5 and below, to maintain caffeine in a solubilized state.

Example 4

4% caffeine (Knoll Pharmaceuticals—BASF) was added to 86 grams of distilled water at room temperature. Various acids as indicated in Table 4 were added at 10% concentration to make a total batch of 100 grams. The results that were obtained are summarized in Table 4 below:

TABLE 4

| Sample | Acid | Wt. ratio xanthine: acid | OBSERVATIONS Initial | 3 days |
|---|---|---|---|---|
| A | Control | | cloudy/precipitate | cloudy/precipitate |
| B | 10% phytic acid (50%) | 0.800 | clear | clear |
| C | 10% L-lactic acid (88%) | 0.455 | clear | clear |
| D | 10% malic and (D-L) | 0.400 | clear | clear |
| E | 10% tartaric acid | 0.400 | clear | clear |
| F | 10% citric acid | 0.400 | clear | large crystals |
| G | 10% glycolic acid (76%) | 0.526 | clear | clear |
| H | 10% phosphoric acid (45%) | 0.889 | cloudy/precipitate | cloudy/precipitate |
| I | 10% HCl (20%) | 2.00 | cloudy/precipitate | cloudy/precipitate |

The results in Table 4 demonstrate that caffeine was solubilized in the presence of an alpha hydroxy acid (Samples C–F) or an inositol phosphoric acid (Sample B), whereas the addition of phosphoric acid or HCl had no effect on caffeine solubility. Note should be taken that in this Example samples contain a relatively high concentration (i.e., 4%) of caffeine.

Example 5

Example 4 was repeated with 10% lactic acid except that pH of the mixtures was varied (using KOH) as indicated in Table 5 below.

TABLE 5

| Sample | Molar ratios lactic/K-lactate | pH | OBSERVATIONS Initial | 3 days |
|---|---|---|---|---|
| A | .125/0 | 2.40 | clear | clear |
| B | 3.5/1 | 3.50 | clear | clear |
| C | 2.0/1 | 4.03 | clear | clear |
| D | 1.75/1 | 5.50 | clear | clear |
| E | 1.2/1.0 | 5.98 | cloudy/ precipitate | cloudy/ |

Example 6

Example 5 was repeated except that 10% phytic acid was employed at various pH. The results that were obtained are summarized in Table 6 below.

TABLE 6

| Sample | Molar ratios phytic/K-phytate | pH | OBSERVATIONS Initial | 3 days |
|---|---|---|---|---|
| A | .0151/0 | .87 | clear | clear |
| B | .280/1 | 1.50 | clear | clear |
| C | .184/1 | 2.67 | clear | clear |
| D | .156/1 | 4.59 | clear | clear |
| E | .142/1 | 5.5 | clear | clear |
| F | .127/1 | 6.5 | cloudy/ precipitate | cloudy/precipitate |

The results in Tables 5 and 6 demonstrate that pH of the inventive compositions is preferably 5.5 or below to maintain caffeine in a solubilized state.

Example 7

Caffeine was added in various amounts as indicated in Table 7 to distilled water containing 10% lactic acid. The weight of each sample was 100 grams. The results that were obtained are summarized in Table 7.

TABLE 7

| Sample | Amount of Caffeine (grams) | Wt. ratio (Caffeine: AHA) | OBSERVATIONS Initial | 3 days |
|---|---|---|---|---|
| A | 30 | 3:1 | cloudy/ precipitate | cloudy/ precipitate |
| B | 20 | 2:1 | Clear | Clear |
| C | 10 | 1:1 | Clear | Clear |
| D | 4 | 0.4:1 | Clear | Clear |
| E | 2 | 0.2:1 | Clear | Clear |
| F | .5 | 0.05:1 | Clear | Clear |
| G | .1 | 0.01:1 | Clear | Clear |
| H | .01 | 0.001:1 | Clear | Clear |

Example 8

Caffeine was added in various amounts to distilled water containing 10% phytic acid. The weight of each sample was 100 grams. The results that were obtained are summarized in Table 8 below:

TABLE 8

| Sample | Amount of Caffeine | wt. ratio | OBSERVATIONS Initial | 3 days |
|---|---|---|---|---|
| A | 30 | 3:1 | cloudy/ precipitate | cloudy/precipitate |
| B | 20 | 2:1 | clear | clear |
| C | 10 | 1:1 | clear | clear |
| D | 4 | 0.4:1 | clear | clear |
| E | 2 | 0.2:1 | clear | clear |
| F | .5 | 0.05:1 | clear | clear |
| G | .1 | 0.01:1 | clear | clear |
| H | .01 | 0.001:1 | clear | clear |

The results in Tables 7 and 8 demonstrate that xanthine::acid ratio employed in the present invention results in solubilized caffeine (Samples B–H) except when the amount of caffeine in a sample is unusually high (e.g., 30% in Sample A), Sample A is outside the scope of the invention.

Example 9

Caffeine was added in various amounts as indicated in Table 9 to distilled water containing either 0.1% lactic acid or 0.1% phytic acid. The results that were obtained are summarized in Table 9 below:

TABLE 9

| Sample | Amount of Caffeine, gr | wt./ratio caffeine:acid | 0.1% lactic acid | 0.1% phytic acid |
|---|---|---|---|---|
| A | .2 | 2:1 | clear | clear |
| B | .3 | 3:1 | clear | clear |
| C | .4 | 4:1 | clear | clear |
| D | .5 | 5:1 | cloudy/ precipitate | cloudy/ precipitate |

The results in Table 9 demonstrate that the ratio of caffeine to acid must be 4:1 or below in order to maintain caffeine in a solubilized state. Sample D is outside the scope of the invention, whereas Samples A–C are within the scope of the invention.

Example 10

The following are typical anti-cellulite gels according to the invention:

| Ingredient | % by weight Example 10A | Example 10B |
|---|---|---|
| alcohol, SD-40B 200 proof | 45 | 45 |
| lactic acid | 5 | 12 |
| butylene glycol | 1.5 | 1.5 |
| tributyl citrate | 1.0 | 1.0 |
| salicylic acid | 1.0 | 1.0 |
| ginkgo biloba extract[1] | 0.5 | 0.5 |
| silver birch extract[1] | 0.5 | 0.5 |
| angelica extract[1] | 0.5 | 0.5 |
| potassium hydroxide | to pH 4.5 | to pH 4.5 |
| Carbowax 300, PEG-6 | 0.5 | 0.5 |
| Hydroxypropyl cellulose | 0.7 | 0.7 |
| caffeine | 0.5 | 0.5 |
| green tea[2] | 0.2 | 0.2 |
| vitamin E acetate | 0.2 | 0.2 |
| vitamin A palmitate | 0.2 | 0.2 |
| $Na_2$ EDTA | 0.1 | 0.1 |
| alpha bisabolol | 0.1 | 0.1 |
| $K_2$ glycyrrhizinate | 0.1 | 0.1 |
| escin | 0.1 | 0.1 |

-continued

| Ingredient | % by weight | |
|---|---|---|
| | Example 10A | Example 10B |
| aslaticoside | 0.01 | 0.01 |
| sericoside | 0.01 | 0.01 |
| water | to 100 | to 100 |

[1] extract obtained from Ichimaru Pharcos
[2] 86% theophylline by weight

Example 11

The following typical skin treatment lotion according to the invention was prepared:

| Ingredient | % by weight |
|---|---|
| lactic acid | 6.00 |
| phytic arid | 6.00 |
| stearic acid | 2.20 |
| glyceryl hydroxystearate | 0.90 |
| Isobutyl stearate | 1.00 |
| Isostearyl palmitate | 1.00 |
| myristyl ether propionate | 1.50 |
| triethanol amine | 1.34 |
| PEG-100 stearate | 1.20 |
| butylene glycol | 2.50 |
| caffeine | 0.50 |
| sorbitan stearate | 0.50 |
| soya sterols | 0.60 |
| tributyl citrate | 0.50 |
| ginkgo biloba extract | 0.50 |
| silver birch extract | 0.50 |
| angelica extract | 0.50 |
| aluminum magnesium silicate | 0.40 |
| dimethicone, 50 cSts | 0.30 |
| myreth-3-myristate | 0.30 |
| vitamin E acetate | 0.20 |
| vitamin A palmitate | 0.20 |
| green tea extract | 0.20 |
| methyl paraben | 0.15 |
| dipotassium glycyrrhizinate | 0.40? |
| alpha bisabolol | 0.40? |
| escin | 0.40? |
| disodium EDTA | 0.05 |
| asiaticoside | 0.01 |
| sericoside | 0.01 |
| potassium hydroxide | to pH 4.5 |
| water | to 100 |

*86% theophylline by weight

Example 12

Clinical studies were performed which assessed changes in appearance of cellulite-affected skin after topical application of a composition according to the invention. Formulae A and B (both within the scope of the invention) were tested in each clinical study. Formulae A and B are described in Table 12.

TABLE 12

| Ingredient | Formula A | Formula B |
|---|---|---|
| Alcohol, SD 40A | 29 | 29 |
| propylene glycol | 3 | 3 |
| caffeine | 3 | 3 |
| glycerin | 2.5 | 2.5 |
| lactic acid | 1.5 | 2.5 |
| malic acid | 1.5 | 2.5 |
| phytic acid | 1.5 | 2.5 |
| angelica extract | 1.0 | 1.0 |
| ginkgo biloba extract | 1.0 | 1.0 |
| silver birch extract | 1.0 | 1.0 |

TABLE 12-continued

| Ingredient | Formula A | Formula B |
|---|---|---|
| green tea[1] | 0.5 | 0.5 |
| carnitine | 0.2 | 0.2 |
| vitamin A acetate | 0.2 | 0.2 |
| vitamin A palmitate | 0.2 | 0.2 |
| epicatechin | 0.1 | 0.1 |
| $K_2$ glycyrrhizinate | 0.1 | 0.1 |
| alpha bisabolol | 0.1 | 0.1 |
| escin | 0.1 | 0.1 |
| sericoside | 0.5 | 0.5 |
| ruscogenin | 0.5 | 0.5 |
| ammonium hydroxide | to pH 4.1 | to pH 4.1 |
| water | to 100 | to 100 |

Each Formula was tested on a separate group of 20 cellulite-affected women; Group A used only Formula A and Group B used only Formula B. The product was applied to one cellulite-affected thigh. Evaluations of treated and untreated thighs were made at 0, 2, 4 and 8 weeks after the start of the treatment. Evaluations were conducted by a clinical evaluator. Evaluators observed the change in such signs of cellulite as lumps, ridges, and dimples, using a scale of 0 to 100, where 0=no dimples, lumps, or ridges. In addition, women self-assessed the differences between treated and untreated legs. Women performed a self-assessment using a grading scale of 1 to 9.

The results that were obtained are summarized in Tables 13–15.

In Table 13, Mean Global Grading result is the mean of measurement of three attributes: lumps, ridges and dimples.

TABLE 13

| | | Mean Global Grading | | | |
|---|---|---|---|---|---|
| | | Treated | | Untreated | |
| Formula | Week | Study I | Study II | Study I | Study II |
| A | 0 | 39.62 | 43.42 | 38.46 | 43.95 |
| | 2 | 35.54 | 39.17* | 33.46 | 45.72 |
| | 4 | 34.46 | 33.89* | 32.69 | 39.61 |
| | 8 | 33.85 | 30.06* | 33.85 | 37.89 |
| B | 0 | 37.54 | 39.21 | 37.77 | 42.37 |
| | 2 | 36.08* | 38.50* | 39.58 | 44.25 |
| | 4 | 31.54* | 33.50* | 38.08 | 37.56 |
| | 8 | 33.08* | 37.88* | 37.31 | 42.44 |

*Significant difference compared to untreated

The results in Table 13 indicate that at least in one study (Study II), significant improvement of cellulite-affected areas resulted from treatment with Formula A compared to untreated thighs. Improvement trend was observed with Formula A at 2 and 4 weeks of treatment in Study I, whereas significant improvement upon treatment with Formula A was observed in Study II.

The results in Table 13 for Study I indicate that the increase in the level of alpha hydroxy acids and phytic acid (Formula B) resulted in significant improvement in the appearance of cellulite-affected areas of skin. Significant improvement upon treatment with Formula B was observed in both studies.

STUDY II:

TABLE 14

| | % Improvement After 8 Weeks | | | | | |
|---|---|---|---|---|---|---|
| | Dimples | | Lumps | | Ridges | |
| Formula | T* | U* | T | U | T | U |
| A | 36 | 54 | 33 | 48 | 37 | 56 |
| B | 30 | 55 | 27 | 40 | 30 | 47 |

*T = Treated; U = Untreated

STUDY II:

TABLE 15

| | Self-Assessment | |
|---|---|---|
| | % Improvement after 8 weeks | |
| Formula | Treated | Untreated |
| A | 22 | 4 |
| B | 30 | 9 |

The results in Tables 14 and 15 for Study II demonstrate significant improvement of cellulite-affected thighs upon treatment with Formula A or Formula B compared to untreated thighs, based both upon clinical evaluation and self-assessment.

Example 13

Formula A (ingredients in Table 12) was evaluated in a self-assessment study by consumers using a commercial anti-cellulite composition (Formula C) as a control.

Each product was tested by a group of 50 cellulite-affected women. Each woman applied the product to both thighs and made comparisons relative to base line. Assessment were made using a scale of 1 to 9. The results that were obtained are summarized in Table 16.

TABLE 16

| Formula | Skin Toned | Smoothness of Skin | Firmness of Skin | Amt. of Ripples | Amt. of Bumps | Amt. of Dimples | Overall Appearance | Severity of Cellulite |
|---|---|---|---|---|---|---|---|---|
| A | 1.45 | 1.06 | 1.31 | −0.92 | −0.88 | −0.90 | −1.14 | −1.49 |
| C | 1.33 | 1.14 | 1.21 | −0.31 | −0.26 | −0.31 | −0.83 | −0.86 |

In Table 16, positive mean values on first 3 attributes indicate improvement in condition. Negative mean values on remainder indicate reduction in signs of cellulite. The results in Table 16 demonstrate that the composition according to the invention performed as well as or better than the commercial anti-cellulite composition in reducing signs of cellulite.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin treatment composition comprising:
   (i) a xanthine in an amount of from about 0.05% to about 20% wherein the xanthine is selected from the group consisting of caffeine, theophylline and mixtures thereof;
   (ii) phytic acid, wherein the weight ratio of xanthine to the acid is from about 2:1 to about 0.001:1; and
   (iii) a cosmetically acceptable vehicle.

2. The composition of claim 1 wherein the pH of the composition is less than or equal to 5.5.

3. The composition of claim 1 wherein the pH of the composition is in the range of from 1.5 to 5.5.

4. The composition of claim 1 wherein the xanthine is present in the amount of at least 0.5%.

5. A method of treating the appearance of flaccid skin or the appearance of cellulite, the method comprising applying topically to skin the composition of claim 1.

6. A skin treatment composition comprising:
   (i) a xanthine in an amount of from about 0.05% to about 20%, wherein the xanthine is selected from the group consisting of caffeine, theophylline and mixtures thereof;
   (ii) an alpha hydroxy acid, wherein the weight ratio of xanthine to the acid is from about 2:1 to about 0.001:1, wherein the α-hydroxy acid is selected from the group consisting of lactic acid, glycolic acid and mixtures thereof; and
   (iii) a cosmetically acceptable vehicle.

7. The composition of claim 6 wherein the pH of the composition is less than or equal to 5.5.

8. The composition of claim 6 wherein the pH of the composition is in the range of from 1.5 to 5.5.

9. The composition of claim 6 wherein the xanthine is present in the amount of at least 0.5%.

10. The composition of claim 6 further comprising phytic acid.

11. A method of treating the appearance of flaccid skin or cellulite, the method comprising applying topically to skin the composition of claim 6.

* * * * *